United States Patent
Neumann et al.

(10) Patent No.: US 8,032,219 B2
(45) Date of Patent: Oct. 4, 2011

(54) CARDIAC PACEMAKER HAVING A SEALED OBLONG HOUSING

(75) Inventors: Andreas Neumann, Berlin (DE);
Thorsten Lewalter, Bonn (DE); Jens Philipp, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 1157 days.

(21) Appl. No.: 11/408,773

(22) Filed: Apr. 21, 2006

(65) Prior Publication Data
US 2006/0241705 A1    Oct. 26, 2006

(30) Foreign Application Priority Data
Apr. 22, 2005    (DE) .......................... 10 2005 020 071

(51) Int. Cl.
*A61N 1/05*    (2006.01)
(52) U.S. Cl. ................ 607/36; 607/32; 607/33; 607/35
(58) Field of Classification Search ................ 607/2, 9, 607/32, 33, 36, 37, 61, 62, 126; 128/903
See application file for complete search history.

(56) References Cited

U.S. PATENT DOCUMENTS

| | | | | |
|---|---|---|---|---|
| 3,943,936 A | * | 3/1976 | Rasor et al. | 607/35 |
| 5,411,535 A | * | 5/1995 | Fujii et al. | 607/32 |
| 6,445,953 B1 | * | 9/2002 | Bulkes et al. | 607/33 |
| 2004/0147973 A1 | * | 7/2004 | Hauser | 607/36 |

FOREIGN PATENT DOCUMENTS

| | | |
|---|---|---|
| EP | 0 916 363 B1 | 5/1999 |
| EP | 1 139 477 A1 | 10/2001 |
| EP | 1 491 235 A2 | 12/2004 |
| WO | WO 90/02581 | 3/1990 |

OTHER PUBLICATIONS

German search report dated Jan. 18, 2006.
European Search Report dated Aug. 29, 2006.

* cited by examiner

*Primary Examiner* — Carl H Layno
*Assistant Examiner* — Pamela M Bays
(74) *Attorney, Agent, or Firm* — Buchanan Ingersoll & Rooney PC (57) ABSTRACT

Endocardial or intravascular cardiac pacemaker having a sealed housing, in which a battery and a pacemaker controller connected to the battery, as well as at least one stimulation pulse generator, are situated, the housing being oblong and having a length of less than 70 mm and a cross-sectional area of less than 100 $mm^2$ and carrying at least two electrodes, each of which has an outwardly directed, electrically conductive surface and is implemented as a stimulation electrode and is at least sometimes electrically connected to the stimulation pulse generator via an electrical connection situated in the interior of the housing.

21 Claims, 10 Drawing Sheets

CARDIAC PACEMAKER HAVING A SEALED OBLONG HOUSING

FIELD OF THE INVENTION

The present invention relates to a cardiac pacemaker, which is implemented to stimulate at least one atrium or one ventricle. The cardiac pacemaker has a sealed housing, in which a battery and a pacemaker controller, a stimulation pulse generator, and a detection stage for cardiac signals are situated, each of which is connected to the battery.

In a preferred variation, however, the present invention also relates to a dual-chamber pacemaker, i.e., a cardiac pacemaker that is capable of stimulating both the atrium and also the ventricle of a heart, preferably the right atrium and the right ventricle.

BACKGROUND OF THE INVENTION

Implantable cardiac pacemakers in their basic known form have housings in which a battery is situated, which allows operation of the pacemaker over many years. The battery powers a pacemaker controller, which is typically connected to a detection stage for cardiac signals and to a stimulation pulse generator. Both the stimulation pulse generator and also the detection stage for cardiac signals are in turn connected to terminals for one or more electrode lines, which allow stimulation pulses generated by the stimulation pulse generator to be delivered to the muscle tissue of the heart (myocardium) or electrical potentials in the heart to be detected and processed.

The different modes of operation and variations of such cardiac pacemakers are known in principle and do not need to be explained further here. The mode of operation of a pacemaker is characterized by a standardized letter code. In the framework of this standardized nomenclature, a DDD pacemaker is a pacemaker which may deliver stimulation pulses to both the ventricle and also to the atrium, which may additionally detect electrical potentials both in the ventricle and also in the atrium, and which finally may be operated inter alia in a demand mode, in which stimulation pulses are only delivered to the ventricle or to the atrium when this is required, i.e., when an electrical potential accompanying a natural contraction of the atrium or ventricle is not detected within a ventricular or atrial escape interval. If a natural cardiac contraction is detected during the duration of the escape interval, the delivery of a corresponding stimulation pulse is suppressed (inhibited). A pacemaker which is capable of stimulating the atrium in the demand mode is referred to as an AAI pacemaker. The first letter describes the capability of the pacemaker of delivering stimulation pulses to the atrium, the second letter describes a capability of the pacemaker of detecting atrial cardiac actions, and the third letter describes the capability of the pacemaker of suppressing the delivery of an atrial stimulation pulse if a natural cardiac action is detected within a set interval, typically referred to as an escape interval. Correspondingly, a pacemaker which may stimulate the ventricle in the demand mode is referred to as a VVI cardiac pacemaker.

Known cardiac pacemakers are typically implanted beneath the clavicle of a patient. The connection to the heart is produced via flexible electrode lines, which end in the particular chamber of the heart (atrium or ventricle) and are provided with electrodes there. On the pacemaker side, the electrode lines are provided with standardized plugs, which engage in similarly standardized sockets of the cardiac pacemaker to produce the desired electrical connection. These sockets of the pacemaker are typically situated in a header of the pacemaker, manufactured from electrically insulating plastic, which is electrically connected via a bushing to the detection stage(s) and the stimulation pulse generator(s) in the interior of a sealed metal housing of the pacemaker. This metal housing additionally houses a battery for operating the pacemaker and control electronics. The stimulation pulse generators typically comprise capacitors in which the energy for a stimulation pulse is stored before delivery of a stimulation pulse. The capacitors are charged with the aid of a suitable charging stage, which acquires its energy from the battery of the pacemaker. Typically, a large part of this metal housing, if not even the largest part of the metal housing, is occupied by the battery of the pacemaker.

The present invention has the object of specifying a cardiac pacemaker which avoids many of the restrictions of the standard arrangement of a pacemaker presented here and thus opens up new fields of application for pacemaker treatment.

SUMMARY OF THE INVENTION

This object is achieved according to the present invention by a cardiac pacemaker of the type cited at the beginning, whose housing is not relatively flat as in known pacemakers, but rather is oblong and is implemented as rod-shaped or cigar-shaped, for example. The cross-sectional area of the housing is less than 100 mm$^2$. The maximum diameter of the housing is 12 mm, so that a cross-sectional shape results whose diameters in different directions do not differ from one another by a factor of more than 2, for example. The length of the housing is at most 70 mm.

Complete functionality of the cardiac pacemaker is ensured with sufficient battery service life at the same time if the housing volume is less than 7 cm$^3$. The largest cross-sectional dimension of the housing of at most 12 mm thus allows a transvenous implantation. It is especially advantageous if the housing has an at least approximately round cross-section. Alternative cross-sectional shapes which are also advantageous would be slightly flattened, nearly circular cross-sections, such as oval or elliptical cross-sections. Polygons having rounded corners also represent a suitable cross-sectional shape.

Furthermore, it is advantageous if the cardiac pacemaker has the same cross-sectional shape over the largest part of its length and, especially advantageously, is cylindrically shaped.

In a preferred embodiment variation, the longitudinal axis of the cardiac pacemaker is linear, but it may also be slightly curved. The radius of curvature is preferably a multiple of the length of the cardiac pacemaker in this case.

The housing carries at least two electrodes, each of which has an electrically conductive surface directed outward and is implemented as a stimulation electrode, as well as being at least temporarily electrically connected to the stimulation pulse generator via an electrical connection situated in the interior of the housing and an electrical switching element. In this context, those electrically conductive components via which stimulation pulses may be delivered or electrical potentials may also be detected, for example, are referred to as electrodes. The electrodes thus form poles for stimulation using their electrically conductive surface. They are integrated into the housing of the cardiac pacemaker according to the present invention.

A cardiac pacemaker of this type has the property of being able to be situated in the auricle of the heart accessible from the right atrium or directly in the ventricle, for example, and, because of the stimulation electrodes situated on its surface, being able to stimulate at least the atrium or the ventricle as an autonomous device.

Preferably, at least the first electrode of the electrodes (poles) has a very small area—i.e., it is punctual, for example—and has a surface area of less than 5 mm². This first electrode is preferably positioned on one longitudinal end of the oblong housing. The second electrode may also have a small area and may have the same shape as the first electrode, for example. Preferably, both electrodes are positioned directly neighboring one another on the same longitudinal end of the housing.

The second electrode may also be formed by a large-area housing part of the housing of the cardiac pacemaker, however, and thus forms an indifferent pole which more or less acts as a neutral electrode.

In an alternative embodiment variation, the electrodes are implemented as annular electrodes which run around the periphery of the housing. In this case as well, the electrodes are preferably positioned closely neighboring one another. In this way, the precise orientation of the cardiac pacemaker after implantation in the right auricle of the heart or even in the ventricle, for example, is relatively noncritical.

The cardiac pacemaker is preferably implemented as a single-chamber demand pacemaker (AAI or VVI). For this purpose, the electrodes advantageously are additionally used as sensing electrodes, which are to be connected at least sometimes to a detection stage in the interior of the housing.

In order to expand the functionality of the cardiac pacemaker, which is autonomous per se, it is advantageous if the cardiac pacemaker has a telemetry transmitter and a telemetry receiver, which are connected to the pacemaker controller and allow operational data of the cardiac pacemaker and detected physiological data, such as intracardial electrocardiograms, to be transmitted to an external device and, vice versa, programming and control commands to be received. Operational parameters, such as a particular stimulation pulse strength to be selected, may also be ascertained in this way using an external device and transmitted to the cardiac pacemaker, so that the operational parameters are also to be stored in a corresponding memory of the pacemaker controller for the further, also autonomous pacemaker operation.

In order to be able to stimulate not only the right atrium, but rather also the right or left ventricle, for example, using a cardiac pacemaker implantable in the heart itself, the cardiac pacemaker preferably has a wired or, even better, wireless interface, which is connected to the pacemaker controller and is implemented to exchange data in regard to the times of events occurring in a particular chamber of the heart (natural or stimulated chamber contractions) with a corresponding interface of a second pacemaker. In this way, a system made of two or more pacemakers is possible, one of which may be placed in atrium and one of which may be placed in the ventricle, and which together have the functionality of a dual-chamber pacemaker. In such a system, the atrial cardiac pacemaker transmits the times of atrial events to the ventricular cardiac pacemaker and vice versa. Therefore, the controller of one cardiac pacemaker may respond to events in the particular other chamber of the heart, i.e., for example, the ventricular cardiac pacemaker may respond to atrial events, so that an atrium-synchronous stimulation of the ventricle, which is known per se, is possible using physiologically adequate atrioventricular delay time (AV interval).

A triple-chamber stimulation in the course of resynchronization therapy is also possible, for example, using more than two intracardially implantable pacemakers of the type according to the present invention.

Instead of implementing a dual-chamber function as described above using two cardiac pacemakers of the type according to the present invention having a data connection to one another, a cardiac pacemaker to be placed in one chamber of the heart may also have an electrode line for a particular other chamber of the heart connected to it. This electrode line is flexible and carries at least one stimulation electrode on its free end or in proximity to its free end. Its length is dimensioned in such a way that it either allows stimulation of the left ventricle via the coronary sinus and possibly a lateral vein branching therefrom or it projects through the right atrium into the right ventricle. An electrode line which is to be inserted into the coronary sinus and into a lateral vein branching from the coronary sinus is preferred. The electrode line is preferably permanently connected to the housing of the cardiac pacemaker and has an electrical conductor in any case which connects the stimulation electrode of the electrode line to the stimulation pulse generator of the cardiac pacemaker. In this way, the cardiac pacemaker becomes a dual-chamber pacemaker, which carries electrodes on its housing for the stimulation of the chamber of the heart in which it is placed in application and which has a flexible electrode line for the stimulation of the other chamber of the heart. In order to allow dual-chamber stimulation, the cardiac pacemaker may have a single stimulation pulse generator, which is to be connected alternately to the atrial stimulation electrode and the ventricular stimulation electrode. Two separate stimulation pulse generators for the atrium and the ventricle may also be provided, which are connected using a line.

In a cardiac pacemaker which has a preferably circular cross-section and whose housing is preferably cylindrically shaped over at least a part of its length, a battery whose cross-section is preferably also round may advantageously be used in a way which exploits the housing volume in the best possible way. This particularly advantageously allows the electrodes of the battery to be coiled in a way known per se. The battery volume to be achieved is between 1 cm³ and 3 cm³. The battery capacitance is preferably between 0.25 and 0.75 Ah.

The housing is preferably formed by housing elements made of metal which are welded to one another. At least one of the electrodes is electrically insulated in relation to the welded metal housing. Of the metal housing elements, one is implemented as tubular having a closed floor, for example. Battery and control electronics may be inserted into this housing element. This advantageously allows the housing to be assembled from three housing elements, for example, namely a central, tubular housing element and two end caps. The stimulation and/or sensing electrodes may then each be positioned between one of the housing caps and the central, tubular housing limit and are also easy to mount at this location.

Alternatively, the housing elements may be manufactured from ceramic or plastic and the electrodes may be formed by metal rings.

The present invention is now to be explained in greater detail on the basis of an exemplary embodiment. Figures are used to illustrate the exemplary embodiment, of which

DETAILED DESCRIPTION OF THE INVENTION

Figure 1:
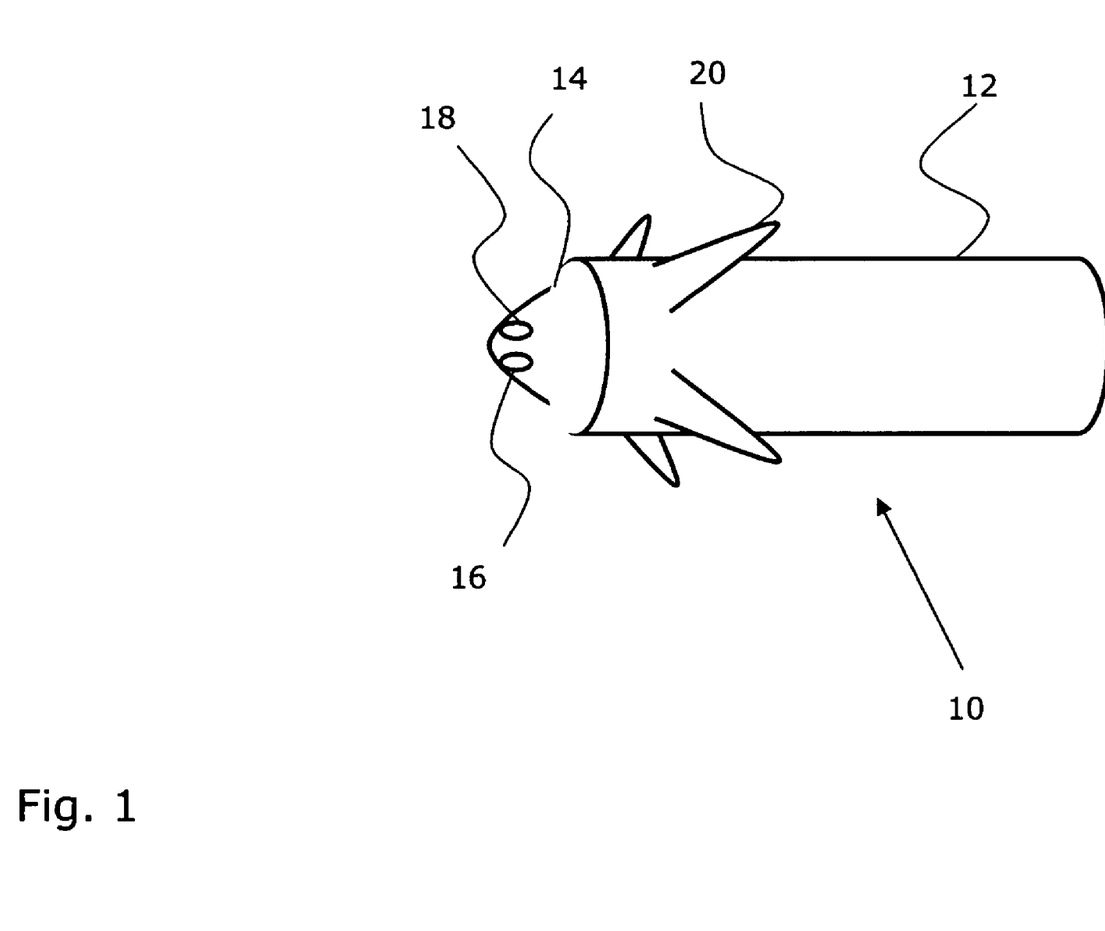
FIG. 1: shows an external view of a first variation of a single-chamber cardiac pacemaker to be implanted in the right auricle of the heart or in the ventricle.

In FIG. 1, a cardiac pacemaker of the type according to the present invention is shown in the form of a single-chamber demand cardiac pacemaker. The cardiac pacemaker 10 has an oblong, cylindrical housing 12 having a semi-spherical housing cap 14. Two small-area stimulation electrodes 16 and 18 are positioned at the tip of the housing cap 14. In order to fix the cardiac pacemaker 10 in a chamber of the heart such as the ventricle or even in the auricle of the right atrium, locking hooks 20 are provided on the housing 12.

The housing 12 is connected to the housing cap 14 to form a seal, so that the space enclosed by the housing 12 and the housing cap 14 is hermetically sealed. The electrodes 16 and 18 are introduced into the housing cap 14 and have electrically conductive surfaces which are electrically insulated in relation to the remaining housing and are used as poles for the stimulation of cardiac tissue.

Figure 2:
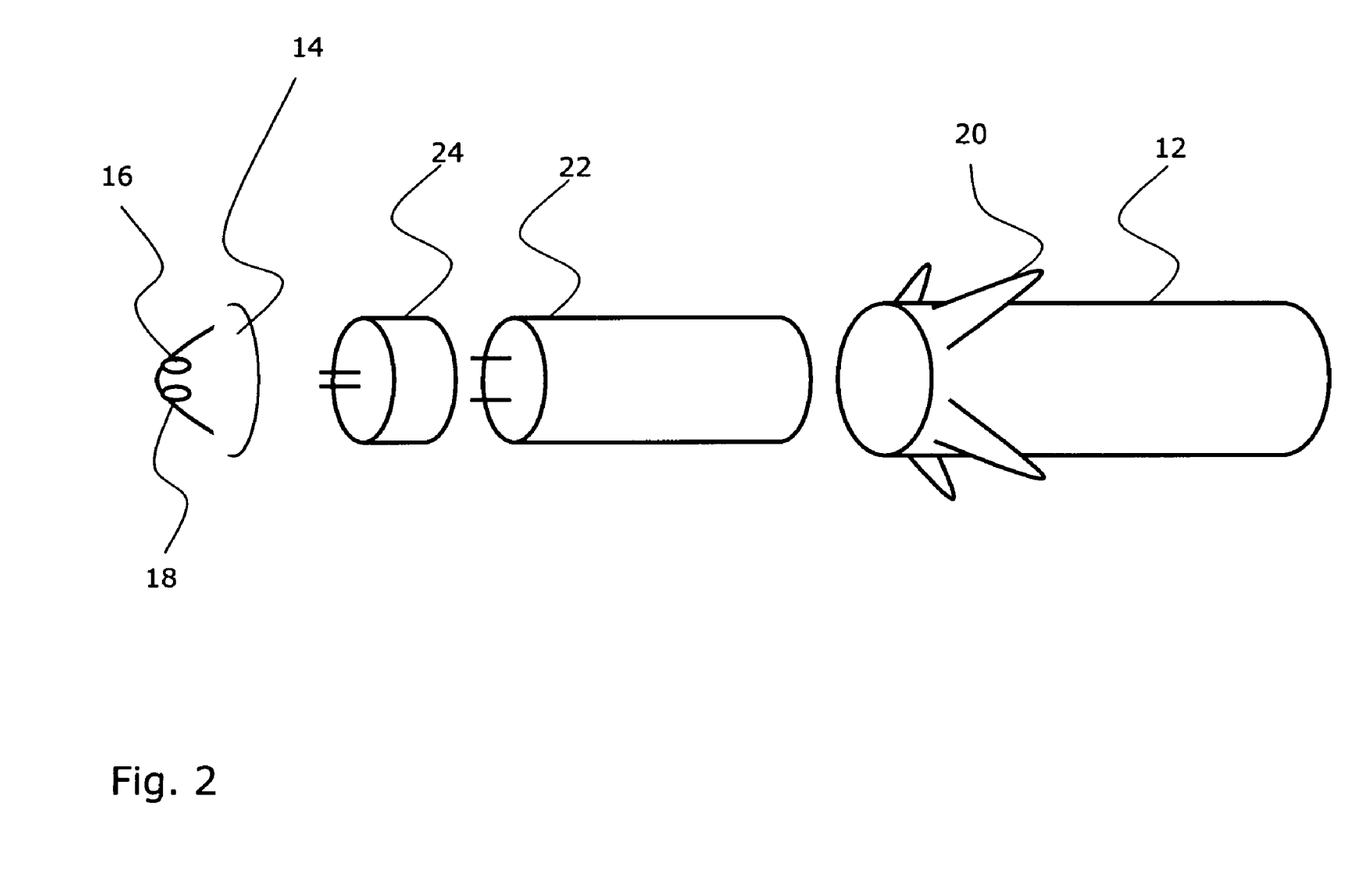
FIG. 2: shows a perspective exploded illustration of the cardiac pacemaker from FIG. 1.

FIG. 2 is an exploded illustration of the cardiac pacemaker 10 from FIG. 1 and shows the components situated in the interior of the housing 12, namely a battery 22 and an electronics module 24. The electronics module 24 comprises an electronic pacemaker controller and at least one stimulation pulse generator and, if the cardiac pacemaker is implemented as a demand pacemaker, additionally a detection stage for cardiac signals. The stimulation pulse generator and the detection state for cardiac signals are each alternately electrically connected to the two electrodes 16 and 18.

Figure 3:
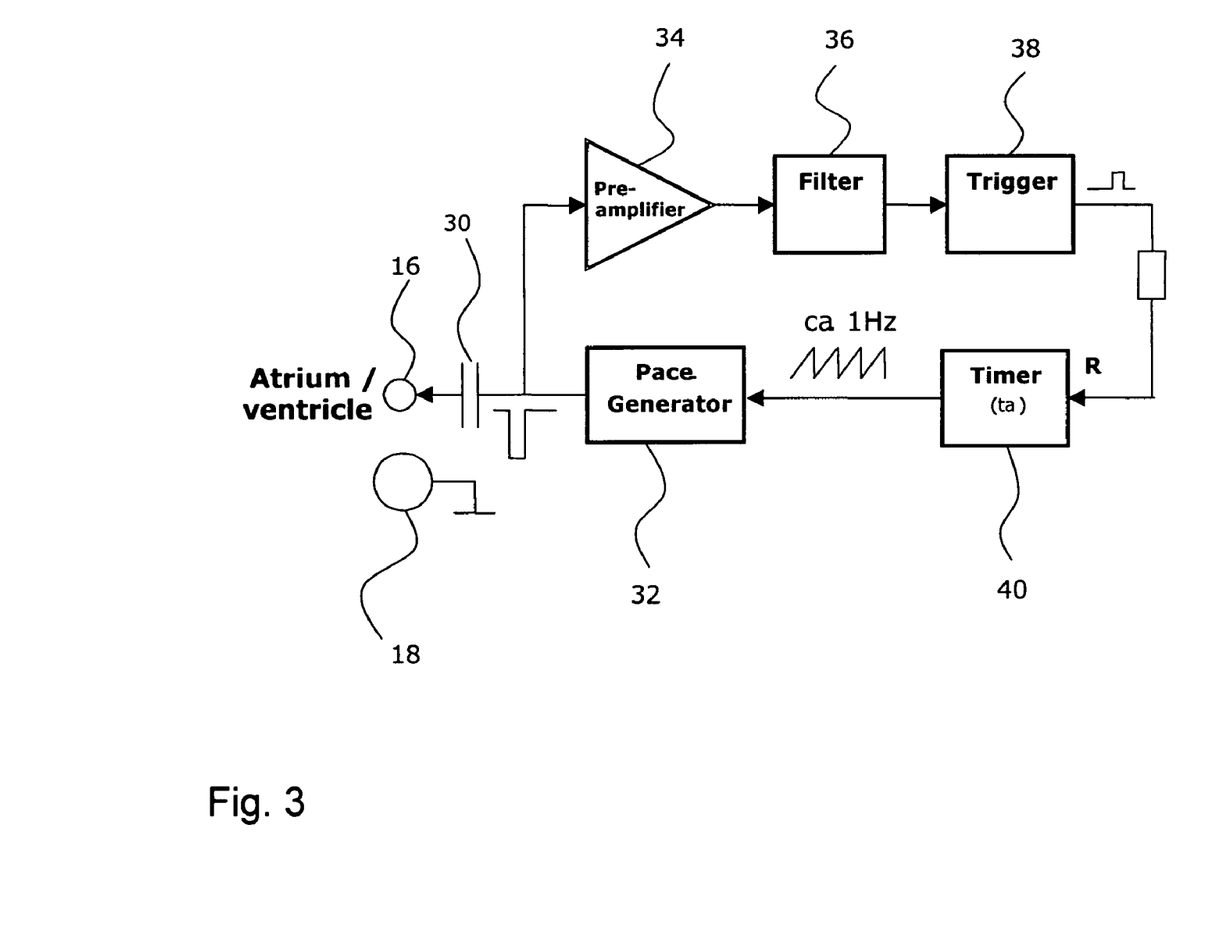
FIG. 3: shows a block diagram of the cardiac pacemaker from FIGS. 1 and 2.

FIG. 3 is a block diagram of the electronics module 24 of a single-chamber demand cardiac pacemaker. The electrode 18 is the reference electrode. The electrode 16 is connected via a coupling capacitor 30 to both a stimulation pulse generator 32 and also a detection stage, which comprises a preamplifier 34, a filter 36, and a trigger 38. The trigger 38 is connected to a timer 40, which is in turn connected to the stimulation pulse generator 32. In the circuit, the trigger 38 has the function of resetting the timer 40. If the timer 40 is not reset, but rather continues to run up to a predefined final value, the timer 40 triggers the delivery of the stimulation pulse via the stimulation pulse generator 32. If the detection stage detects a natural chamber contraction via the preamplifier 34 and the filter 36 before expiration of the timer 40, the trigger 38 delivers a pulse which resets the timer 40 and in this way prevents the timer 40 from expiring and triggering a stimulation pulse. If no natural chamber contractions are detected, the timer expires normally and then resets itself, so that it outputs stimulation pulses at a set stimulation rate. The stimulation rate may be predefined telemetrically via a pacemaker controller not shown in greater detail in FIG. 3, for example. However, the stimulation rate may also be tailored to the physiological requirements of the patient with the aid of a physiological sensor. A rate-adaptive pacemaker results in this way.

Figure 4:
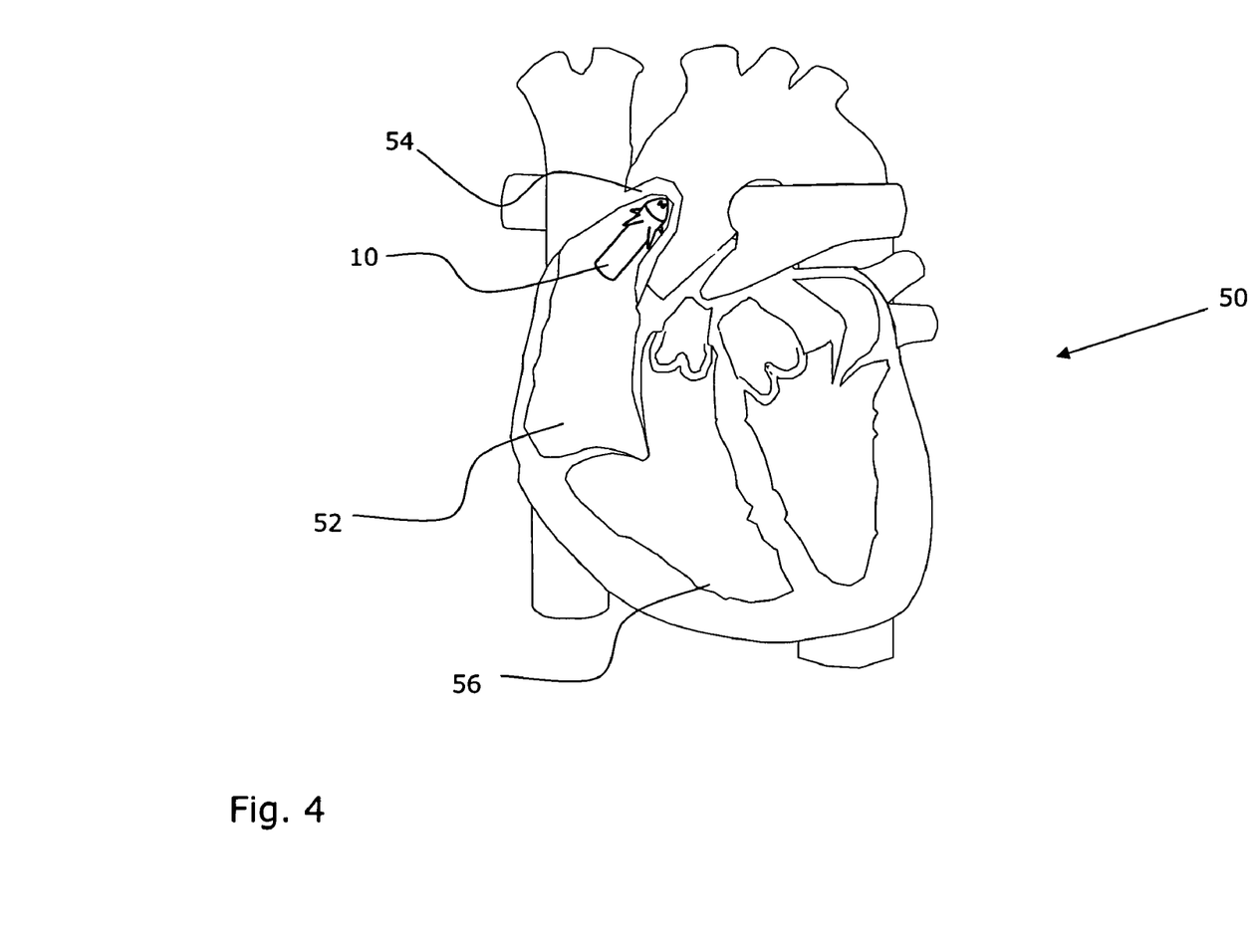
FIG. 4: shows the arrangement of the cardiac pacemaker from FIGS. 1 and 2 as an AAI cardiac pacemaker in the right auricle of the heart.

FIG. 4 shows the arrangement of the pacemaker from FIGS. 1 and 2 in the right auricle of the heart 54, branching from the right atrium 52 of a human heart 50. In this form, the cardiac pacemaker 10 operates as an AAI pacemaker.

Figure 5:
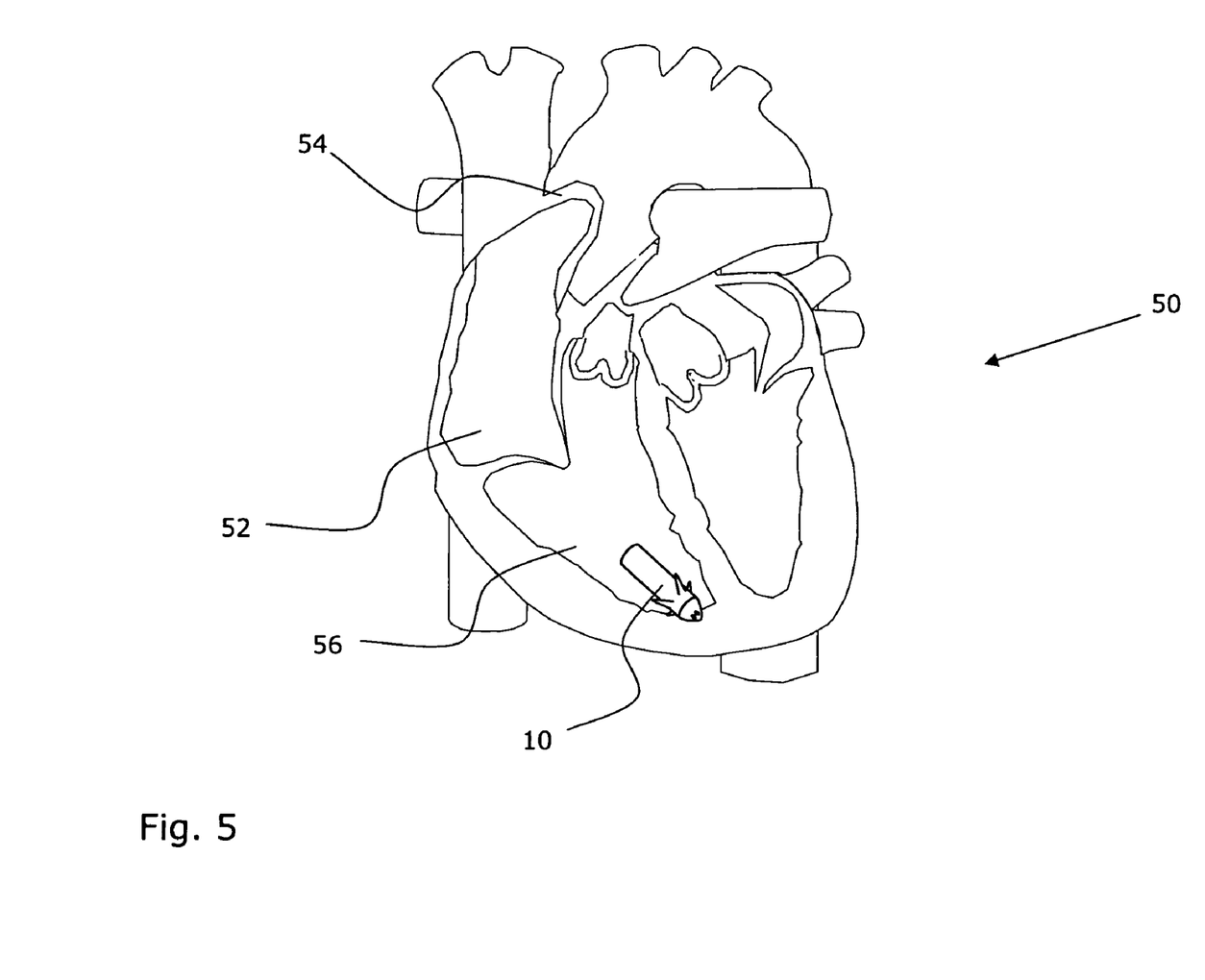
FIG. 5: shows the arrangement of the cardiac pacemaker from FIGS. 1 and 2 as a VVI cardiac pacemaker in the right ventricle.

However, as FIG. 5 shows, the cardiac pacemaker 10 may also be situated in the right ventricle 56 of the heart 50 and then operates as a VVI pacemaker.

Figure 6:
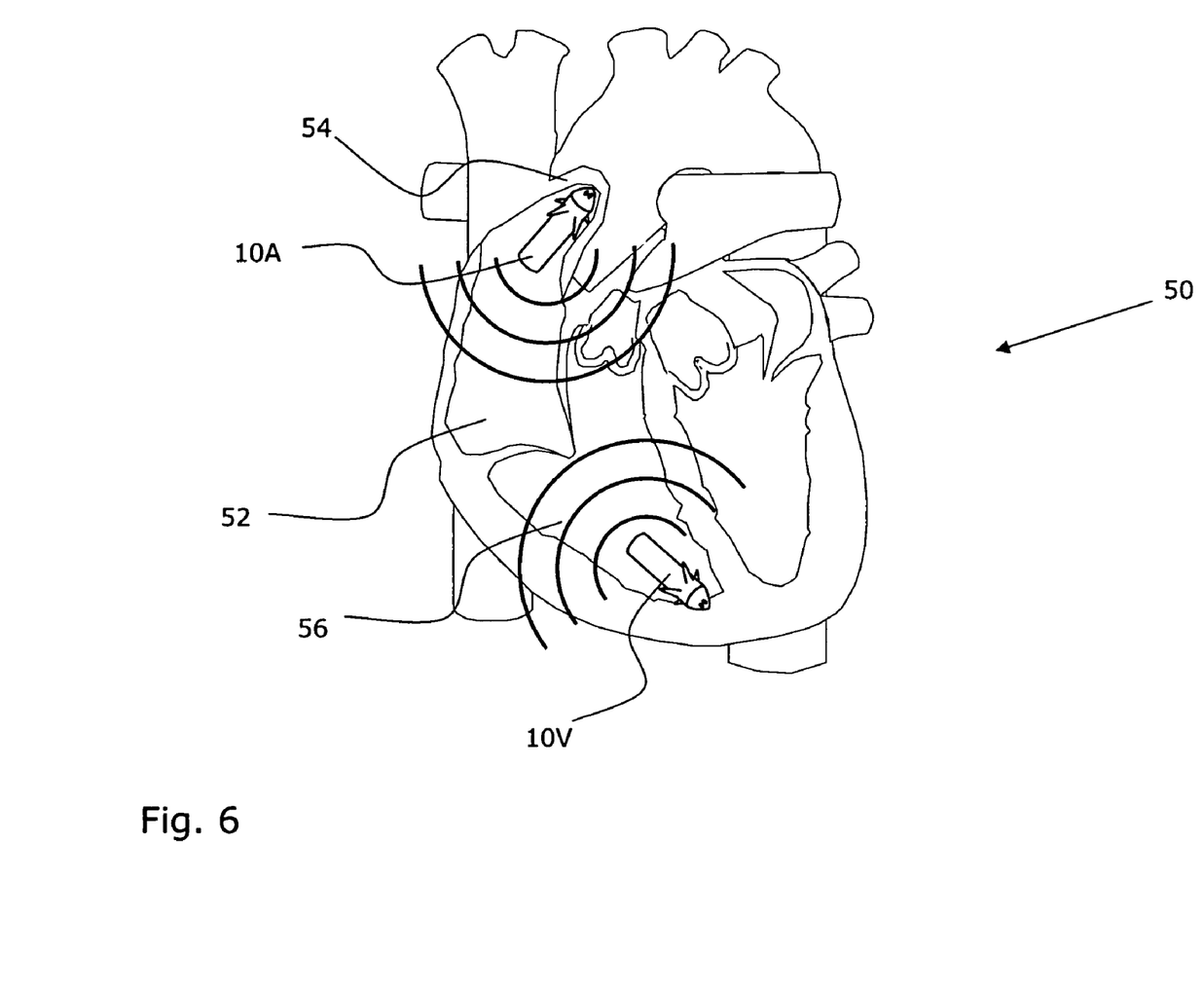
FIG. 6: shows a dual-chamber pacemaker system formed by two implanted cardiac pacemakers.
Figure 7:
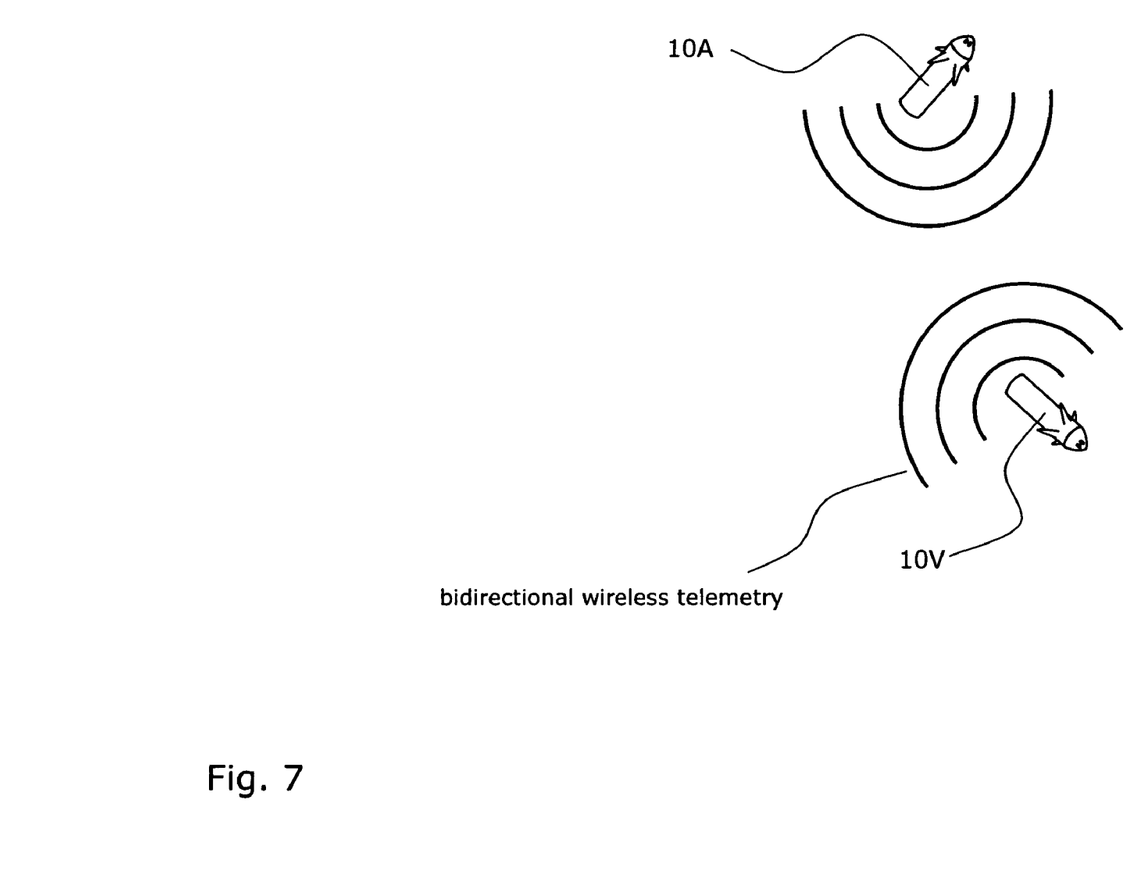
FIG. 7: shows the system from FIG. 6 in the non-implanted state.
Figure 8:
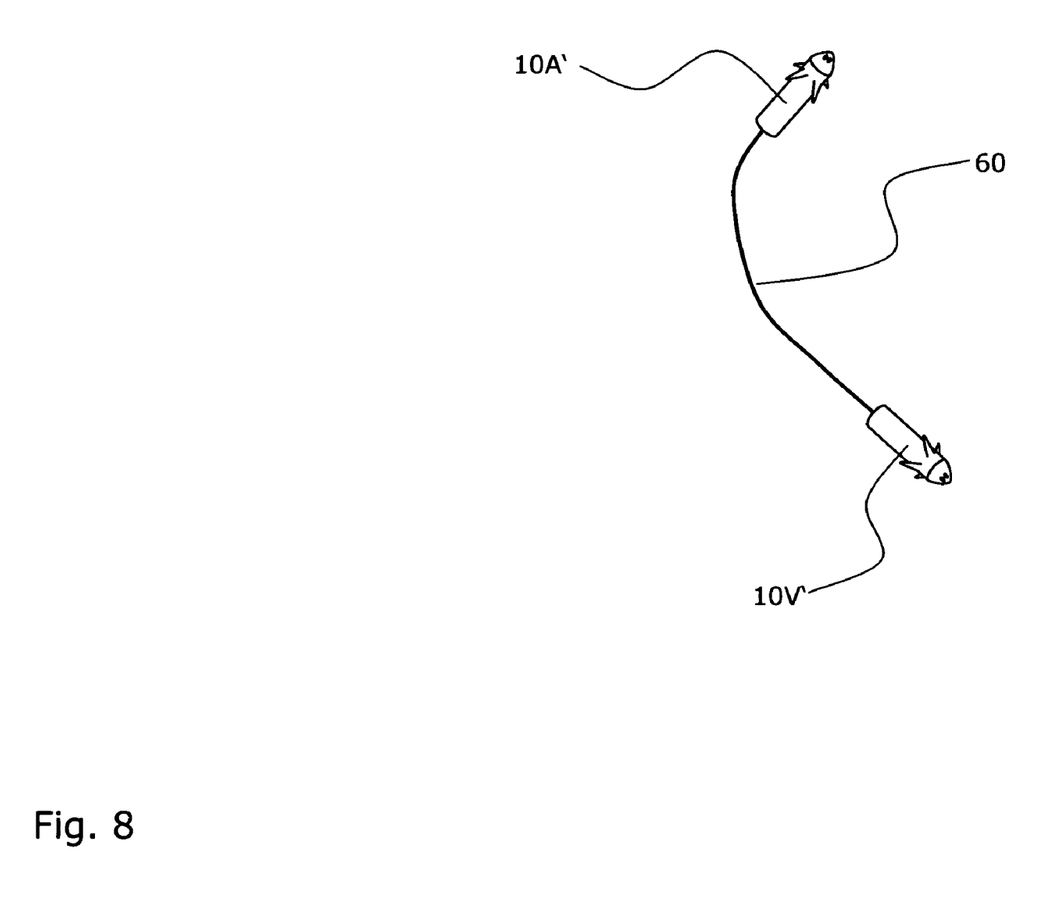
FIG. 8: shows the system from FIGS. 6 and 7 having a wired instead of a wireless bidirectional telemetric connection.

As already noted above, the electronics module 24 of a particular pacemaker may have a wired or, even better, wireless interface to one or more further pacemakers of the same type, so that two or more pacemakers may jointly form a multichamber pacemaker system, as is shown in FIGS. 6 through 8. A dual-chamber system is shown in FIG. 6. A first pacemaker 10A is situated in the right auricle of the right atrium 52, while a second cardiac pacemaker 10V is situated in the right ventricle 56 of the heart 50. The system formed by two pacemakers 10A and 10V, each having a wireless interface, is shown once again in FIG. 7. FIG. 8 shows a less preferred variation, in which the cardiac pacemakers 10A' and 10V' are connected to one another via a wire 60 and corresponding wired interfaces.

Figure 9:
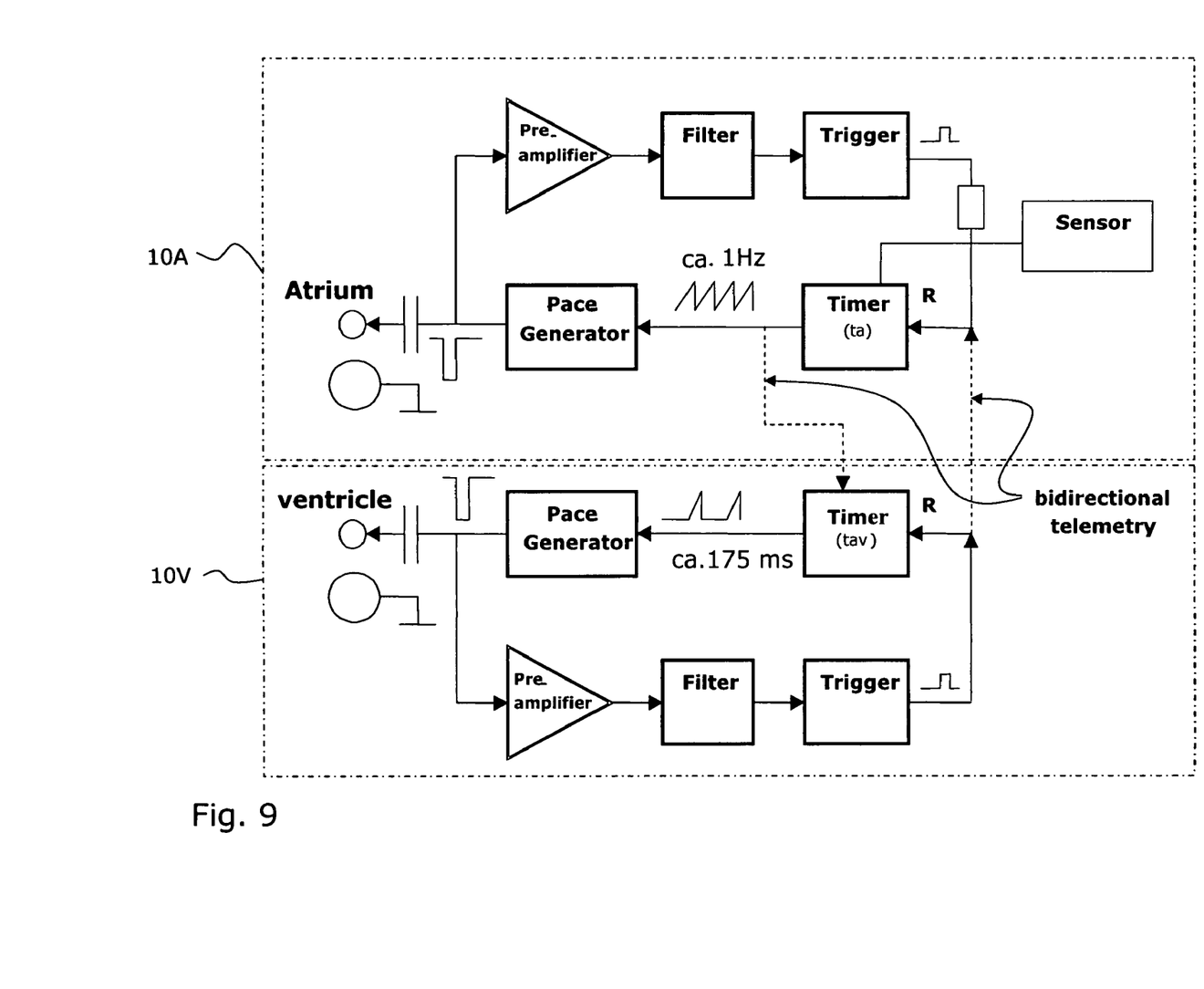
FIG. 9: shows a block diagram of the dual-chamber pacemaker system formed by cardiac pacemakers like 10A and 10V.

FIG. 9 shows a block diagram of the dual-chamber pacemaker system formed by cardiac pacemakers like 10A and 10V. The block diagram is a block diagram of a typical dual-chamber cardiac pacemaker, which is distributed to two housings in the present case, however. These housings are indicated by a dot-dashed line in each case. The upper part of the block diagram represents the part which is to be assigned to the cardiac pacemaker 10A to be placed in the atrium, while the lower part of the block diagram represents the circuit of the cardiac pacemaker 10V to be placed in the ventricle. The circuit of the cardiac pacemaker 10A and the circuit of the cardiac pacemaker 10V are connected to one another via appropriate wireless interfaces, such as a bidirectional, wireless telemetry link. This is illustrated in the block diagram by dashed lines. In this way, an AV timer in the ventricular cardiac pacemaker 10V may be triggered by the detection of an atrial event or by the delivery of an atrial stimulation pulse, while, vice versa, the detection of a ventricular event triggers the timer for the delivery of the atrial stimulation pulse. Furthermore, it is to be noted that the sensor for the physiological requirements of the patient which was already noted in connection with FIG. 3 is indicated in FIG. 9.

Figure 10:
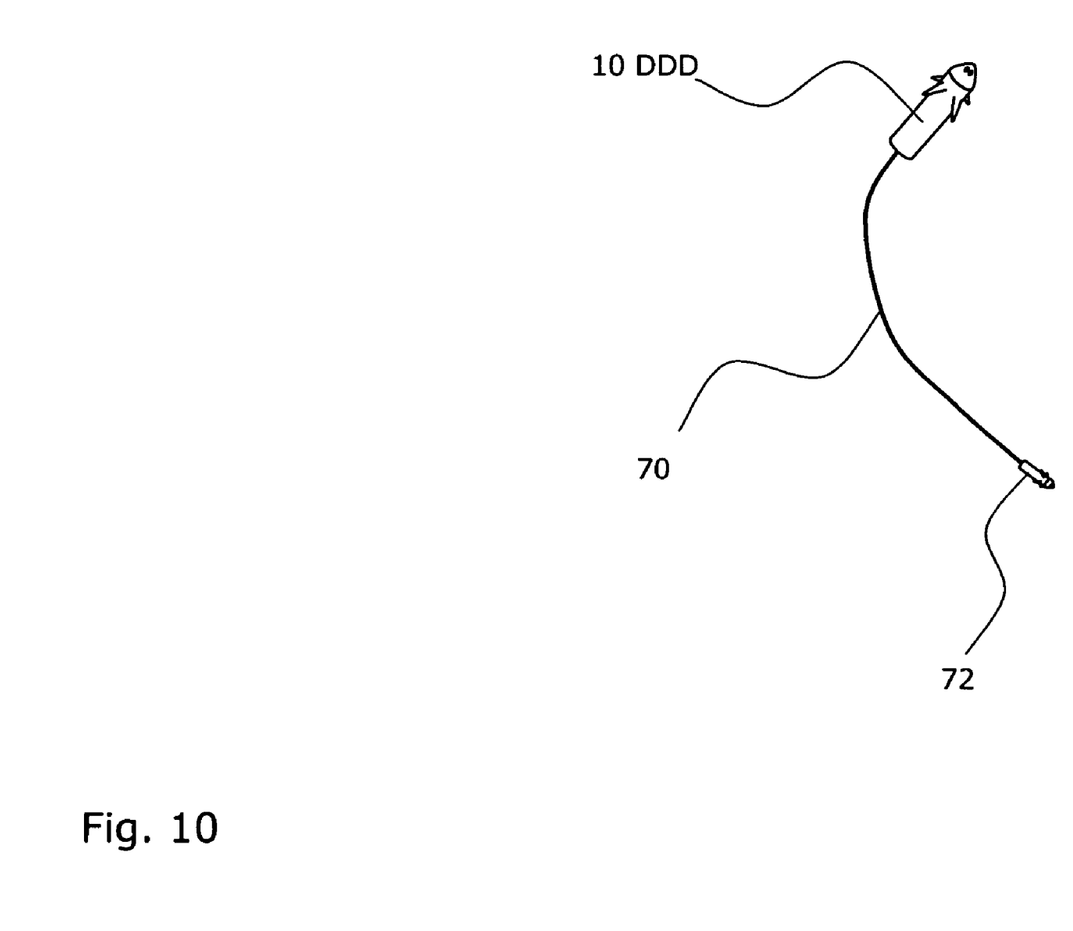
FIG. 10: shows an alternative intracardially implantable dual-chamber cardiac pacemaker.

Finally, FIG. 10 shows a variation of a dual-chamber cardiac pacemaker 10DDD, in which all of the electronics shown in FIG. 9 are housed in a housing which is to be implanted in the auricle of the right atrium, for example. The telemetry link is then replaced by a wired connection. A flexible electrode line 70 is attached to this cardiac pacemaker 10DDD, which carries a bipolar electrode head 72 on its end, which is to be placed in the apex of the right ventricle. The electrode line 70 is correspondingly dimensioned in such way that it bridges the distance from the right auricle of the heart up to the apex of the right ventricle. The cardiac pacemaker 10DDD shown in FIG. 10 is thus also completely implantable endocardially and/or intravascularly.

We claim:

1. An endocardial or intravascular cardiac pacemaker having a sealed housing, in which
a battery and
a pacemaker controller connected to the battery and at least one stimulation pulse generator are situated, characterized in that
the housing is oblong and
has a length of less than 70 mm and
a cross-sectional area of less than 100 mm$^2$ and
carries at least two electrodes,
each of which has an outwardly directed, electrically conductive surface and
is implemented as a stimulation electrode and
is electrically connected to the stimulation pulse generator via an electrical connection positioned in the interior of the housing
wherein the electrodes have an area of less than 5 mm$^2$ and are positioned directly neighboring one another on a cap of the same longitudinal end of the housing.

2. The cardiac pacemaker according to claim 1, characterized in that the cross-sectional dimension of the housing is at most 12 mm.

3. The cardiac pacemaker according to claim 1, characterized in that the housing volume is at most 7 cm$^3$.

4. The cardiac pacemaker according to claim 1, characterized in that the housing has an at least approximately circular cross-section.

5. The cardiac pacemaker according to claim 4, characterized in that the housing is cylindrically shaped over the largest part of its length.

6. The cardiac pacemaker according to claim 4, characterized in that the battery has an at least approximately circular cross-section.

7. The cardiac pacemaker according to claim 6, characterized in that the battery has coiled electrodes.

8. The cardiac pacemaker according to claim 1, characterized in that the cardiac pacemaker is implemented for implantation in the heart.

9. The cardiac pacemaker according to claim 8, characterized in that the cardiac pacemaker is implemented for implantation in the auricle of the heart.

10. The cardiac pacemaker according to claim 8, characterized in that the cardiac pacemaker is implemented for implantation in the ventricle.

11. The cardiac pacemaker according to claim 1, characterized in that at least one electrode is implemented as an annular electrode, which runs around the periphery of the housing.

12. The cardiac pacemaker according to claim 1, characterized in that a detection stage for cardiac signals is positioned in the housing and the electrodes are additionally implemented as sensing electrodes and can be connected to the detection stage.

13. The cardiac pacemaker according to claim 1, characterized in that the cardiac pacemaker has a telemetry transceiver, which is connected to the pacemaker controller and is implemented for transmitting operational data and physiological data and for receiving programming and/or control commands and/or operational parameters.

14. The cardiac pacemaker according to claim 1, characterized in that the cardiac pacemaker has a wired or a wireless interface, which is connected to the pacemaker controller and is implemented for exchanging data with a corresponding interface of a second cardiac pacemaker.

15. A system made of two or more cardiac pacemakers according to claim 14, which form a multichamber pacemaker system together.

16. The cardiac pacemaker according to claim 1, characterized by a flexible electrode line, connected to the housing, which carries at least one stimulation electrode on its free end or in proximity to its free end and has an electrical conductor which connects the stimulation electrode to the stimulation pulse generator.

17. The cardiac pacemaker according to claim 1, characterized in that the battery has a capacitance between 0.25 Ah and 0.75 Ah.

18. The cardiac pacemaker according to claim 1, characterized in that the battery occupies a volume between 1 cm$^3$ and 3 cm$^3$.

19. The cardiac pacemaker according to claim 1, characterized in that the housing is formed by metal housing elements which are welded to one another and are insulated at least in relation to the electrodes.

20. The cardiac pacemaker according to claim 19, characterized in that at least one of the housing elements is implemented as tubular.

21. The cardiac pacemaker according to claim 1, characterized in that the housing is formed by housing elements made of electrically insulating materials such as plastic or ceramic.

* * * * *